US00PP20064P2

(12) United States Plant Patent
Jandrew

(10) Patent No.: US PP20,064 P2
(45) Date of Patent: Jun. 9, 2009

(54) ***BRACTEANTHA* PLANT NAMED 'STABUR YEL'**

(50) Latin Name: *Bracteantha bracteata*
Varietal Denomination: Stabur Yel

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/150,467

(22) Filed: Apr. 28, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
(74) *Attorney, Agent, or Firm*—C. A. Whealy

(57) ABSTRACT

A new and distinct cultivar of *Bracteantha* plant named 'Stabur Yel', characterized by its upright, compact, bushy and rounded uniform plant habit; freely branching habit; freely flowering habit; large inflorescences with numerous bright yellow-colored involucral bracts; strong peduncles that hold the inflorescences above the foliar plane; and good garden performance.

1 Drawing Sheet

Botanical designation: *Bracteantha bracteata.*
Cultivar denomination: 'Stabur Yel'.

BACKGROUND OF THE INVENTION

The present invention relates to a new and distinct cultivar of *Bracteantha* plant, botanically known as *Bracteantha bracteata,* and hereinafter referred to by the name 'Stabur Yel'.

The new *Bracteantha* is a product of a planned breeding program conducted by the Inventor in Gilroy, Calif. The objective of the program is to create and develop new *Bracteantha* cultivars with uniform plant habit, freely flowering habit and attractive inflorescence coloration.

The new *Bracteantha* originated from a cross-pollination by the Inventor in May, 2005 of a proprietary selection of *Bracteantha bracteata* identified as code number 340-2, not patented, as the female, or seed, parent with a proprietary selection of *Bracteantha bracteata* identified as code number 320-1, as the male, or pollen, parent. The new *Bracteantha* was discovered and selected by the Inventor as a single flowering plant within the progeny of the stated cross-pollination in a controlled greenhouse environment in Gilroy, Calif. in December, 2005. The selection of this plant was based on its uniform plant habit, freely flowering habit and attractive inflorescence coloration.

Asexual reproduction of the new *Bracteantha* by vegetative cuttings in a controlled greenhouse environment in Gilroy, Calif. since December, 2005, has shown that the unique features of this new *Bracteantha* are stable and reproduced true to type in successive generations.

SUMMARY OF THE INVENTION

The cultivar Stabur Yel has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Stabur Yel'. These characteristics in combination distinguish 'Stabur Yel' as a new and distinct cultivar of *Bracteantha:*

1. Upright, compact, bushy and rounded uniform plant habit.
2. Freely branching habit.
3. Freely flowering habit.
4. Large inflorescences with numerous bright yellow-colored involucral bracts.
5. Strong peduncles that hold the inflorescences above the foliar plane.
6. Good garden performance.

Plants of the new *Bracteantha* differ from plants of the female parent selection in the following characteristics:

1. Plants of the new *Bracteantha* have narrower leaves than plants of the female parent selection.
2. Plants of the new *Bracteantha* are more freely flowering than plants of the female parent selection.
3. Plants of the new *Bracteantha* have larger inflorescences than plants of the female parent selection.

Plants of the new *Bracteantha* differ from plants of the male parent selection in the following characteristics:

1. Plants of the new *Bracteantha* have darker colored leaves than plants of the male parent selection.
2. Plants of the new *Bracteantha* are more freely flowering than plants of the male parent selection.
3. Plants of the new *Bracteantha* have larger inflorescences than plants of the male parent selection.

Plants of the new *Bracteantha* can be compared to plants of the *Bracteantha* named 'OHB003790', disclosed in U.S. Plant Pat. No. 15,629. In side-by-side comparisons conducted in Gilroy, Calif., plants of the new *Bracteantha* differed from plants of 'OHB003790' in the following characteristics:

1. Plants of the new *Bracteantha* had larger inflorescences than plants of 'OHB003790'.

2. Inflorescences of plants of the new *Bracteantha* had more involucral bracts than inflorescences of plants of 'OHB003790'.
3. Involucral bracts of plants of the new *Bracteantha* were brighter yellow in color than involucral bracts of plants of 'OHB003790'.

BRIEF DESCRIPTION OF THE PHOTOGRAPH

The accompanying photograph illustrates the overall appearance of the new *Bracteantha*. This photograph shows the colors as true as it is reasonably possible to obtain in colored reproductions of this type. Colors in the photograph may differ slightly from the color values cited in the detailed botanical description which accurately describe the colors of the new *Bracteantha*. The photograph comprises a top perspective view of a typical flowering plant of 'Stabur Yel' grown in a container. Plants used in the aforementioned photograph were grown in Gilroy, Calif. during the summer for three months in 10-cm containers in a greenhouse and under conditions and practices which approximate those generally used in commercial *Bracteantha* production. During the production of the plants, day temperatures ranged from 24° C. to 32° C. and night temperatures averaged 18° C.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Gilroy, Calif. during the summer in ground beds in an outdoor nursery and under conditions and practices which approximate those generally used in commercial *Bracteantha* production. During the production of the plants, day temperatures ranged from 24° C. to 32° C. and night temperatures averaged 18° C. Measurements and numerical values represent averages for typical flowering plants. Plants were four months old when the description was taken.

Botanical classification: *Bracteantha bracteata* 'Stabur Yel'.

Parentage:

*Female, or seed, parent.*—Proprietary selection of *Bracteantha bracteata* identified as code number 340-2, not patented.

*Male, or pollen, parent.*—Proprietary selection of *Bracteantha bracteata* identified as code number 320-1, not patented.

Propagation:

*Type.*—Vegetative cuttings.

*Time to initiate and develop roots.*—About three to four weeks at 20° C. to 23° C.

*Root description.*—Fibrous; white in color.

Plant description:

*Plant form/growth habit.*—Upright, compact and rounded uniform plant habit with dense and bushy foliage and inflorescences held above the foliage on strong peduncles. Vigorous growth habit.

*Plant height.*—About 21 cm to 25 cm.

*Plant diameter or spread.*—About 27 cm to 32 cm.

*Lateral branches.*—Quantity per plant: Freely branching habit with about five to eight lateral branches developing per plant; pinching enhances lateral branch development. Length: About 5 cm to 10 cm. Diameter: About 7 mm to 8.5 mm. Internode length: About 1.3 cm to 1.7 cm. Aspect: Mostly upright. Strength: Strong. Texture: Hirsute. Color: Close to 146C.

*Foliage description.*—Arrangement: Alternate, simple; sessile. Length: About 7.2 cm to 9.2 cm. Width: About 1.5 cm to 2.1 cm. Shape: Lanceolate. Apex: Acute. Base: Obtuse. Margin: Entire. Texture, upper and lower surfaces: Hirsute. Venation pattern: Pinnate. Color: Developing foliage, upper surface: Close to 137A. Developing foliage, lower surface: Close to 137B. Fully expanded foliage, upper surface: Close to 147A; venation, close to 144C. Fully expanded foliage, lower surface: Close to 137A; venation, close to 144C.

Inflorescence description:

*Appearance.*—Rotate composite inflorescence form. Involucral bracts and disc florets developing acropetally on a capitulum. Large inflorescences positioned above the foliage on strong peduncles. Terminal and axillary inflorescences face mostly upright. Freely flowering habit; about 26 to 32 inflorescences develop per plant per plant. Inflorescences persistent.

*Fragrance.*—None detected.

*Time to flower.*—Plants flower continuously throughout the spring and summer in California.

*Post-production longevity.*—Inflorescences maintain good substance for about three to four weeks on the plant.

*Inflorescence bud.*—Height: About 1.5 cm to 2 cm. Diameter: About 8 mm to 13 mm. Shape: Oblate. Color: Close to 7A.

*Inflorescence size.*—Diameter: About 6.5 cm to 7.5 cm. Depth (height): About 2.5 cm. Disc diameter: About 1.5 cm.

*Involucral bracts.*—Shape: Elliptical. Length, largest bracts: About 1.3 cm to 1.4 cm. Width, largest bracts: About 6 mm to 7 mm. Apex: Acute. Base: Attenuate. Margin: Entire. Texture, upper and lower surfaces: Smooth, glabrous; stiff, papery. Number of involucral bracts per inflorescence: About 200 in about ten to twelve whorls. Color: When opening and fully opened, upper surface: Close to 2A to slightly darker than 2A. When opening and fully opened, lower surface: Close to 2A to slightly darker than 2A.

*Disc florets.*—Arrangement: Massed in the center of the receptacle with one whorl of about 20 filiform florets (close to 1C in color) at the perimeter of the disc florets. Shape: Tubular; apex dentate, five-pointed. Length: About 1.1 cm. Diameter: About 1 mm. Number of disc florets per inflorescence: About 200 in numerous tight whorls. Color: Close to N25A; towards the base, close to 1C.

*Phyllaries.*—Quantity per inflorescence: About 20. Length: About 1 cm. Width: About 2 mm. Shape: Linear. Apex: Acuminate. Base: Truncate, fused. Margin: Entire. Texture, upper and lower surfaces: Smooth. Color, upper and lower surfaces: Close to 137A.

*Peduncles.*—Length: About 5.5 cm to 8 cm. Diameter: About 3 mm to 4 mm. Strength: Strong. Aspect: Mostly upright. Texture: Hirsute. Color: Close to 146C.

*Reproductive organs (present on disc florets only).*—Androecium: Arrangement: Fused anther tubes with five anthers surrounding the style. Anther length: Less than 1 mm. Anther color: Close to 17B. Pollen amount: Moderate. Pollen color: Close to 17C. Gynoecium (present on disc and filiform florets):

Quantity per floret: One. Pistil length: About 1 cm to 1.1 cm. Stigma shape: Bi-parted. Stigma color: Close to 21A. Style color: Close to 1C.

*Seeds/fruits.*—Seed and fruit production has not been observed on plants of the new *Bracteantha.*

Disease/pest resistance: Plants of the new *Bracteantha* have not been shown to be resistant to pathogens and pests common to *Bracteanthas.*

Garden performance: Plants of the new *Bracteantha* have been observed to have good garden performance and to tolerate rain, wind and temperatures ranging from about 4° C. to about 36° C.

It is claimed:

1. A new and distinct *Bracteantha* plant named 'Stabur Yel' as illustrated and described.

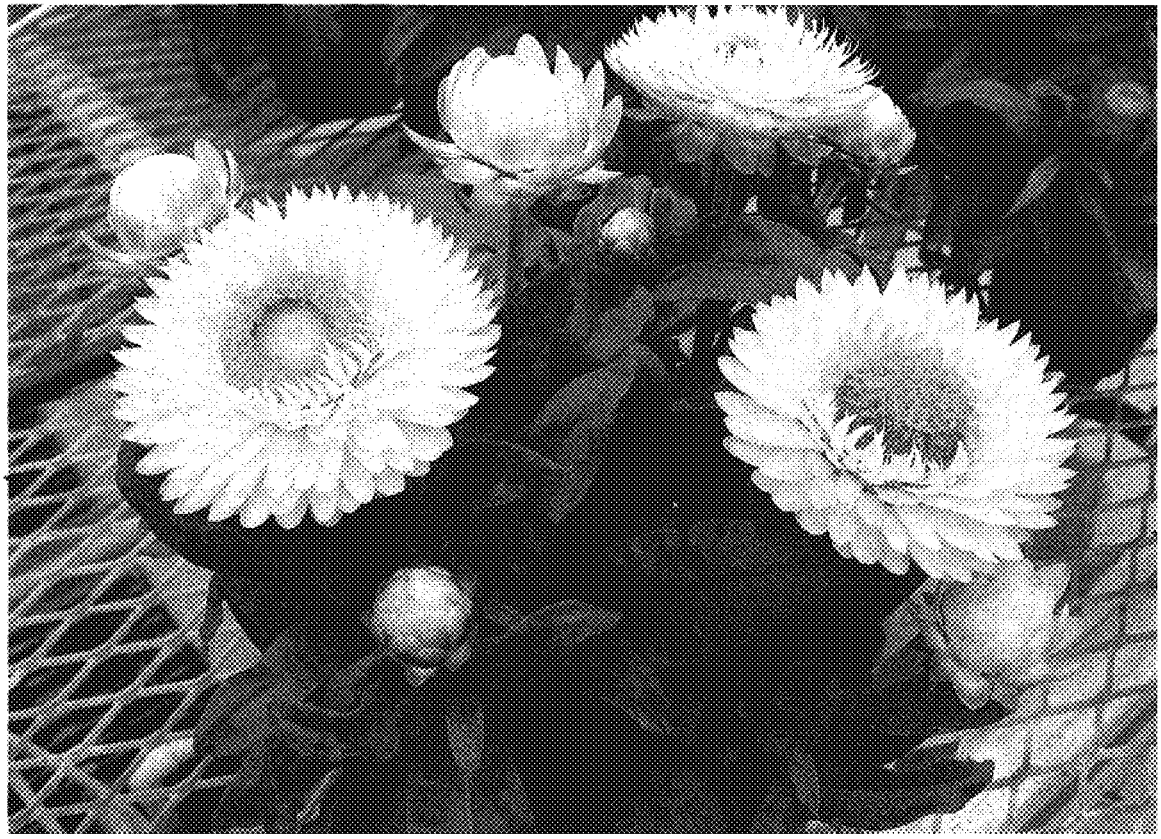

* * * * *